(12) United States Patent
Hans et al.

(10) Patent No.: US 7,982,020 B2
(45) Date of Patent: Jul. 19, 2011

(54) VARIANT POLYNUCLEOTIDE FOR INCREASING L-PROLINE PRODUCTION

(75) Inventors: Stephan Hans, Osnabrueck (DE); Brigitte Bathe, Salzkotten (DE); Georg Thierbach, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 164 days.

(21) Appl. No.: 11/722,301

(22) PCT Filed: Dec. 13, 2005

(86) PCT No.: PCT/EP2005/013372
§ 371 (c)(1),
(2), (4) Date: Oct. 31, 2008

(87) PCT Pub. No.: WO2006/066758
PCT Pub. Date: Jun. 29, 2006

(65) Prior Publication Data
US 2009/0221043 A1    Sep. 3, 2009

(30) Foreign Application Priority Data
Dec. 22, 2004    (DE) .......................... 10 2004 061 696

(51) Int. Cl.
*C07H 21/04*    (2006.01)

(52) U.S. Cl. ...................................... 536/23.1

(58) Field of Classification Search ............. None
See application file for complete search history.

(56) References Cited

FOREIGN PATENT DOCUMENTS
WO    2004 069996    8/2004

OTHER PUBLICATIONS

Cerdeno-Tarraga et al, The complete genome sequence and analysis of *Corynebacterium diphtheriae* NCTC13129. Nucleic Acids Res. 31 (22), 6516-6523 (2003).*
GenBank database Acc# NP_940115 from Cerdeno-Tarraga et al, The complete genome sequence and analysis of *Corynebacterium diphtheriae* NCTC13129. Nucleic Acids Res. 31 (22), 6516-6523 (2003).*
GenBank database Acc# NP_940115 from Cerdeno-Tarraga et al, The complete genome sequence and analysis of *Corynebacterium diphtheriae* NCTC13129. Nucleic Acids Res. 31 (22), 6516-6523 (2003). Alignment with SEQID No. 2.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Cerdano-Tarraga A.M., et al., "The Complete Genome Sequence and Analysis of *Corynebacterium diphtheriae* NCTC13129". Nucleic Acids Research, vol. 31, No, 22, XP 002373890, 2003.
Immacolata Massarelli, et al.. "Enhanced and Feedback-Resistant Gamma-Glutamyl Kinase Activity of an *Escherichia coli* Transformant Carrying a Mutated Prob Gene of *Streptococcus thermophilus*", FEMS Microbiology Letters, vol. 182, No. 1, XP 002373888, pp. 143-147, 2000.

* cited by examiner

*Primary Examiner* — Sheridan Swope
(74) *Attorney, Agent, or Firm* — Oblon, Spivak, McClelland, Maier & Neustadt, L.L.P.

(57) ABSTRACT

The invention relates to mutated variants of the proB gene from coryneform bacteria, which encode γ-glutamyl kinase, and to processes for fermentative production of L-proline using bacteria which contain this mutation.

8 Claims, No Drawings

SEQUENCE LISTING

```
<160> NUMBER OF SEQ ID NOS: 6

<210> SEQ ID NO 1
<211> LENGTH: 1110
<212> TYPE: DNA
<213> ORGANISM: Coryneform bacterium
<220> FEATURE:
<221> NAME/KEY: CDS
<222> LOCATION: (1)..(1107)
<220> FEATURE:
<221> NAME/KEY: misc_feature
<222> LOCATION: (149)..(149)
<223> OTHER INFORMATION: 'Xaa' at location 149 stands for Lys, Asn, Arg,
      Ser, Thr, Ile, Met, Glu, Asp, Ala, Val, Gln, His, Pro, Leu, Tyr,
      Trp, Cys, or Phe
```

```
<220> FEATURE:
<221> NAME/KEY: misc_feature
<222> LOCATION: (445)..(447)
<223> OTHER INFORMATION: Xaa all proteinogenic amino acids other than
      glycine

<400> SEQUENCE: 1 atg cgt gag cgc atc tcc aac gct aag cga gtg gtg gtg aaa att ggt      48
Met Arg Glu Arg Ile Ser Asn Ala Lys Arg Val Val Val Lys Ile Gly
 1               5                  10                  15 tcg tcc tca ttg act aac gat gag gac gga cac acc gtc gat ccc aac      96
Ser Ser Ser Leu Thr Asn Asp Glu Asp Gly His Thr Val Asp Pro Asn
             20                  25                  30 cgc atc aac act att gtc aat gcc ttg caa gca cgc atg gaa gct ggc     144
Arg Ile Asn Thr Ile Val Asn Ala Leu Gln Ala Arg Met Glu Ala Gly
         35                  40                  45 tcg gac ctc atc gtt gtg tcc tct ggc gca gtg gcc gcg gga atg gcc     192
Ser Asp Leu Ile Val Val Ser Ser Gly Ala Val Ala Ala Gly Met Ala
 50                  55                  60 ccg ctt gga ttg agc acc cgg ccc acg gaa ttg gca gtc aag cag gct     240
Pro Leu Gly Leu Ser Thr Arg Pro Thr Glu Leu Ala Val Lys Gln Ala
 65                  70                  75                  80 gca gca gca gtg ggg caa gtt cac ctc atg cac cag tgg gga cgt tct     288
Ala Ala Ala Val Gly Gln Val His Leu Met His Gln Trp Gly Arg Ser
                 85                  90                  95 ttt gcc cgg tat ggt cgc ccc atc ggc cag gtg ctt ctt acc gca gct     336
Phe Ala Arg Tyr Gly Arg Pro Ile Gly Gln Val Leu Leu Thr Ala Ala
             100                 105                 110 gat gca gga aag cgt gat cgt gcg agg aat gcg cag cgt acc atc gac     384
Asp Ala Gly Lys Arg Asp Arg Ala Arg Asn Ala Gln Arg Thr Ile Asp
         115                 120                 125 aag ctg cgc att ttg ggc gcg gtt cct atc gtc aat gaa aat gac acc     432
Lys Leu Arg Ile Leu Gly Ala Val Pro Ile Val Asn Glu Asn Asp Thr
130                 135                 140 gtg gca acc acc nnn gtg aat ttt ggt gac aac gac cga ctt gct gca     480
Val Ala Thr Thr Xaa Val Asn Phe Gly Asp Asn Asp Arg Leu Ala Ala
145                 150                 155                 160 att gtg gcg cac ctg gtg tcg gct gat gct ttg gtg ctg ctc agt gac     528
Ile Val Ala His Leu Val Ser Ala Asp Ala Leu Val Leu Leu Ser Asp
                 165                 170                 175 gtg gat gga ctt ttt gat aaa aac cct act gat ccc acc gcg aag ttt     576
Val Asp Gly Leu Phe Asp Lys Asn Pro Thr Asp Pro Thr Ala Lys Phe
             180                 185                 190 att tcc gag gtt cgt gac ggc aat gat ttg aaa ggt gtc att gcc ggc     624
Ile Ser Glu Val Arg Asp Gly Asn Asp Leu Lys Gly Val Ile Ala Gly
         195                 200                 205 gac ggc gga aaa gtg ggc acc ggt ggc atg gca tca aag gtg tct gct     672
Asp Gly Gly Lys Val Gly Thr Gly Gly Met Ala Ser Lys Val Ser Ala
     210                 215                 220 gca cgt ttg gct tcc cga agt ggc gtg cct gtg ctg ttg acc tct gcg     720
Ala Arg Leu Ala Ser Arg Ser Gly Val Pro Val Leu Leu Thr Ser Ala
225                 230                 235                 240 gca aac att ggc cca gca ctg gaa gac gcc cag gtg ggc act gta ttc     768
Ala Asn Ile Gly Pro Ala Leu Glu Asp Ala Gln Val Gly Thr Val Phe
                 245                 250                 255 cac ccc aag gac aac cgc ctc tcc gcg tgg aag ttc tgg gct ttg tat     816
His Pro Lys Asp Asn Arg Leu Ser Ala Trp Lys Phe Trp Ala Leu Tyr
             260                 265                 270 gcc gca gat act gca gga aag atc cga ctc gat gac ggc gcg gtg gaa     864
Ala Ala Asp Thr Ala Gly Lys Ile Arg Leu Asp Asp Gly Ala Val Glu
         275                 280                 285
```

```
gca gtg acc tcc ggt ggt aaa tct ttg ctg gct gtg ggc att act gaa      912
Ala Val Thr Ser Gly Gly Lys Ser Leu Leu Ala Val Gly Ile Thr Glu
    290             295                 300 atc att ggt gat ttc cag cag ggt gag atc gtg gag atc ttg gga cct      960
Ile Ile Gly Asp Phe Gln Gln Gly Glu Ile Val Glu Ile Leu Gly Pro
305             310                 315                 320 gcc ggc caa atc atc ggg cga ggc gag gtg tcc tac gat tct gat acc     1008
Ala Gly Gln Ile Ile Gly Arg Gly Glu Val Ser Tyr Asp Ser Asp Thr
                325                 330                 335 ttg caa tca atg gtt ggt atg caa acg cag gac ctt cca gat ggc atg     1056
Leu Gln Ser Met Val Gly Met Gln Thr Gln Asp Leu Pro Asp Gly Met
            340                 345                 350 cag cgc ccg gta gtg cat gca gat tat ctg tcc aac tac gcc agc cgc     1104
Gln Arg Pro Val Val His Ala Asp Tyr Leu Ser Asn Tyr Ala Ser Arg
        355                 360                 365 gcg taa                                                              1110
Ala

<210> SEQ ID NO 2
<211> LENGTH: 369
<212> TYPE: PRT
<213> ORGANISM: Coryneform bacterium
<220> FEATURE:
<221> NAME/KEY: misc_feature
<222> LOCATION: (149)..(149)
<223> OTHER INFORMATION: The 'Xaa' at location 149 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 2

Met Arg Glu Arg Ile Ser Asn Ala Lys Arg Val Val Lys Ile Gly
1               5                   10                  15

Ser Ser Ser Leu Thr Asn Asp Glu Asp Gly His Thr Val Asp Pro Asn
            20                  25                  30

Arg Ile Asn Thr Ile Val Asn Ala Leu Gln Ala Arg Met Glu Ala Gly
            35                  40                  45

Ser Asp Leu Ile Val Val Ser Ser Gly Ala Val Ala Ala Gly Met Ala
    50                  55                  60

Pro Leu Gly Leu Ser Thr Arg Pro Thr Glu Leu Ala Val Lys Gln Ala
65              70                  75                  80

Ala Ala Ala Val Gly Gln Val His Leu Met His Gln Trp Gly Arg Ser
                85                  90                  95

Phe Ala Arg Tyr Gly Arg Pro Ile Gly Gln Val Leu Leu Thr Ala Ala
            100                 105                 110

Asp Ala Gly Lys Arg Asp Arg Ala Arg Asn Ala Gln Arg Thr Ile Asp
        115                 120                 125

Lys Leu Arg Ile Leu Gly Ala Val Pro Ile Val Asn Glu Asn Asp Thr
    130                 135                 140

Val Ala Thr Thr Xaa Val Asn Phe Gly Asp Asn Asp Arg Leu Ala Ala
145                 150                 155                 160

Ile Val Ala His Leu Val Ser Ala Asp Ala Leu Val Leu Leu Ser Asp
                165                 170                 175

Val Asp Gly Leu Phe Asp Lys Asn Pro Thr Asp Pro Thr Ala Lys Phe
            180                 185                 190

Ile Ser Glu Val Arg Asp Gly Asn Asp Leu Lys Gly Val Ile Ala Gly
        195                 200                 205

Asp Gly Gly Lys Val Gly Thr Gly Gly Met Ala Ser Lys Val Ser Ala
    210                 215                 220

Ala Arg Leu Ala Ser Arg Ser Gly Val Pro Val Leu Leu Thr Ser Ala
```

```
                225                 230                 235                 240
Ala Asn Ile Gly Pro Ala Leu Glu Asp Ala Gln Val Gly Thr Val Phe
                245                 250                 255

His Pro Lys Asp Asn Arg Leu Ser Ala Trp Lys Phe Trp Ala Leu Tyr
                260                 265                 270

Ala Ala Asp Thr Ala Gly Lys Ile Arg Leu Asp Asp Gly Ala Val Glu
                275                 280                 285

Ala Val Thr Ser Gly Gly Lys Ser Leu Leu Ala Val Gly Ile Thr Glu
                290                 295                 300

Ile Ile Gly Asp Phe Gln Gln Gly Glu Ile Val Glu Ile Leu Gly Pro
305                 310                 315                 320

Ala Gly Gln Ile Ile Gly Arg Gly Glu Val Ser Tyr Asp Ser Asp Thr
                325                 330                 335

Leu Gln Ser Met Val Gly Met Gln Thr Gln Asp Leu Pro Asp Gly Met
                340                 345                 350

Gln Arg Pro Val Val His Ala Asp Tyr Leu Ser Asn Tyr Ala Ser Arg
                355                 360                 365

Ala

<210> SEQ ID NO 3
<211> LENGTH: 1110
<212> TYPE: DNA
<213> ORGANISM: Coryneform bacterium
<220> FEATURE:
<221> NAME/KEY: CDS
<222> LOCATION: (1)..(1107)
<220> FEATURE:
<221> NAME/KEY: mutation
<222> LOCATION: (446)..(446)
<223> OTHER INFORMATION: adenine

<400> SEQUENCE: 3 atg cgt gag cgc atc tcc aac gct aag cga gtg gtg gtg aaa att ggt       48
Met Arg Glu Arg Ile Ser Asn Ala Lys Arg Val Val Val Lys Ile Gly
1               5                   10                  15 tcg tcc tca ttg act aac gat gag gac gga cac acc gtc gat ccc aac       96
Ser Ser Ser Leu Thr Asn Asp Glu Asp Gly His Thr Val Asp Pro Asn
                20                  25                  30 cgc atc aac act att gtc aat gcc ttg caa gca cgc atg gaa gct ggc      144
Arg Ile Asn Thr Ile Val Asn Ala Leu Gln Ala Arg Met Glu Ala Gly
            35                  40                  45 tcg gac ctc atc gtt gtg tcc tct ggc gca gtg gcc gcg gga atg gcc      192
Ser Asp Leu Ile Val Val Ser Ser Gly Ala Val Ala Ala Gly Met Ala
        50                  55                  60 ccg ctt gga ttg agc acc cgg ccc acg gaa ttg gca gtc aag cag gct      240
Pro Leu Gly Leu Ser Thr Arg Pro Thr Glu Leu Ala Val Lys Gln Ala
65                  70                  75                  80 gca gca gca gtg ggg caa gtt cac ctc atg cac cag tgg gga cgt tct      288
Ala Ala Ala Val Gly Gln Val His Leu Met His Gln Trp Gly Arg Ser
                85                  90                  95 ttt gcc cgg tat ggt cgc ccc atc ggc cag gtg ctt ctt acc gca gct      336
Phe Ala Arg Tyr Gly Arg Pro Ile Gly Gln Val Leu Leu Thr Ala Ala
                100                 105                 110 gat gca gga aag cgt gat cgt gcg agg aat gcg cag cgt acc atc gac      384
Asp Ala Gly Lys Arg Asp Arg Ala Arg Asn Ala Gln Arg Thr Ile Asp
            115                 120                 125 aag ctg cgc att ttg ggc gcg gtt cct atc gtc aat gaa aat gac acc      432
Lys Leu Arg Ile Leu Gly Ala Val Pro Ile Val Asn Glu Asn Asp Thr
        130                 135                 140 gtg gca acc acc gat gtg aat ttt ggt gac aac gac cga ctt gct gca      480
Val Ala Thr Thr Asp Val Asn Phe Gly Asp Asn Asp Arg Leu Ala Ala
```

```
Val Ala Thr Thr Asp Val Asn Phe Gly Asp Asn Asp Arg Leu Ala Ala
145                 150                 155                 160 att gtg gcg cac ctg gtg tcg gct gat gct ttg gtg ctg ctc agt gac      528
Ile Val Ala His Leu Val Ser Ala Asp Ala Leu Val Leu Leu Ser Asp
                165                 170                 175 gtg gat gga ctt ttt gat aaa aac cct act gat ccc acc gcg aag ttt      576
Val Asp Gly Leu Phe Asp Lys Asn Pro Thr Asp Pro Thr Ala Lys Phe
                180                 185                 190 att tcc gag gtt cgt gac ggc aat gat ttg aaa ggt gtc att gcc ggc      624
Ile Ser Glu Val Arg Asp Gly Asn Asp Leu Lys Gly Val Ile Ala Gly
                195                 200                 205 gac ggc gga aaa gtg ggc acc ggt ggc atg gca tca aag gtg tct gct      672
Asp Gly Gly Lys Val Gly Thr Gly Gly Met Ala Ser Lys Val Ser Ala
        210                 215                 220 gca cgt ttg gct tcc cga agt ggc gtg cct gtg ctg ttg acc tct gcg      720
Ala Arg Leu Ala Ser Arg Ser Gly Val Pro Val Leu Leu Thr Ser Ala
225                 230                 235                 240 gca aac att ggc cca gca ctg gaa gac gcc cag gtg ggc act gta ttc      768
Ala Asn Ile Gly Pro Ala Leu Glu Asp Ala Gln Val Gly Thr Val Phe
                245                 250                 255 cac ccc aag gac aac cgc ctc tcc gcg tgg aag ttc tgg gct ttg tat      816
His Pro Lys Asp Asn Arg Leu Ser Ala Trp Lys Phe Trp Ala Leu Tyr
                260                 265                 270 gcc gca gat act gca gga aag atc cga ctc gat gac ggc gcg gtg gaa      864
Ala Ala Asp Thr Ala Gly Lys Ile Arg Leu Asp Asp Gly Ala Val Glu
                275                 280                 285 gca gtg acc tcc ggt ggt aaa tct ttg ctg gct gtg ggc att act gaa      912
Ala Val Thr Ser Gly Gly Lys Ser Leu Leu Ala Val Gly Ile Thr Glu
        290                 295                 300 atc att ggt gat ttc cag cag ggt gag atc gtg gag atc ttg gga cct      960
Ile Ile Gly Asp Phe Gln Gln Gly Glu Ile Val Glu Ile Leu Gly Pro
305                 310                 315                 320 gcc ggc caa atc atc ggg cga ggc gag gtg tcc tac gat tct gat acc     1008
Ala Gly Gln Ile Ile Gly Arg Gly Glu Val Ser Tyr Asp Ser Asp Thr
                325                 330                 335 ttg caa tca atg gtt ggt atg caa acg cag gac ctt cca gat ggc atg     1056
Leu Gln Ser Met Val Gly Met Gln Thr Gln Asp Leu Pro Asp Gly Met
                340                 345                 350 cag cgc ccg gta gtg cat gca gat tat ctg tcc aac tac gcc agc cgc     1104
Gln Arg Pro Val Val His Ala Asp Tyr Leu Ser Asn Tyr Ala Ser Arg
        355                 360                 365 gcg taa                                                              1110
Ala

<210> SEQ ID NO 4
<211> LENGTH: 369
<212> TYPE: PRT
<213> ORGANISM: Coryneform bacterium

<400> SEQUENCE: 4

Met Arg Glu Arg Ile Ser Asn Ala Lys Arg Val Val Lys Ile Gly
1               5                   10                  15

Ser Ser Ser Leu Thr Asn Asp Glu Asp Gly His Thr Val Asp Pro Asn
                20                  25                  30

Arg Ile Asn Thr Ile Val Asn Ala Leu Gln Ala Arg Met Glu Ala Gly
            35                  40                  45

Ser Asp Leu Ile Val Val Ser Ser Gly Ala Val Ala Ala Gly Met Ala
        50                  55                  60

Pro Leu Gly Leu Ser Thr Arg Pro Thr Glu Leu Ala Val Lys Gln Ala
65                  70                  75                  80
```

Ala Ala Ala Val Gly Gln Val His Leu Met His Gln Trp Gly Arg Ser
            85                  90                  95

Phe Ala Arg Tyr Gly Arg Pro Ile Gly Gln Val Leu Leu Thr Ala Ala
            100                 105                 110

Asp Ala Gly Lys Arg Asp Arg Ala Arg Asn Ala Gln Arg Thr Ile Asp
            115                 120                 125

Lys Leu Arg Ile Leu Gly Ala Val Pro Ile Val Asn Glu Asn Asp Thr
130                 135                 140

Val Ala Thr Thr Asp Val Asn Phe Gly Asp Asn Asp Arg Leu Ala Ala
145                 150                 155                 160

Ile Val Ala His Leu Val Ser Ala Asp Ala Leu Val Leu Leu Ser Asp
            165                 170                 175

Val Asp Gly Leu Phe Asp Lys Asn Pro Thr Asp Pro Thr Ala Lys Phe
            180                 185                 190

Ile Ser Glu Val Arg Asp Gly Asn Asp Leu Lys Gly Val Ile Ala Gly
            195                 200                 205

Asp Gly Gly Lys Val Gly Thr Gly Gly Met Ala Ser Lys Val Ser Ala
            210                 215                 220

Ala Arg Leu Ala Ser Arg Ser Gly Val Pro Val Leu Leu Thr Ser Ala
225                 230                 235                 240

Ala Asn Ile Gly Pro Ala Leu Glu Asp Ala Gln Val Gly Thr Val Phe
            245                 250                 255

His Pro Lys Asp Asn Arg Leu Ser Ala Trp Lys Phe Trp Ala Leu Tyr
            260                 265                 270

Ala Ala Asp Thr Ala Gly Lys Ile Arg Leu Asp Asp Gly Ala Val Glu
            275                 280                 285

Ala Val Thr Ser Gly Gly Lys Ser Leu Leu Ala Val Gly Ile Thr Glu
            290                 295                 300

Ile Ile Gly Asp Phe Gln Gln Gly Glu Ile Val Glu Ile Leu Gly Pro
305                 310                 315                 320

Ala Gly Gln Ile Ile Gly Arg Gly Glu Val Ser Tyr Asp Ser Asp Thr
            325                 330                 335

Leu Gln Ser Met Val Gly Met Gln Thr Gln Asp Leu Pro Asp Gly Met
            340                 345                 350

Gln Arg Pro Val Val His Ala Asp Tyr Leu Ser Asn Tyr Ala Ser Arg
            355                 360                 365

Ala

<210> SEQ ID NO 5
<211> LENGTH: 1110
<212> TYPE: DNA
<213> ORGANISM: Coryneform bacterium
<220> FEATURE:
<221> NAME/KEY: CDS
<222> LOCATION: (1)..(1107)
<220> FEATURE:
<221> NAME/KEY: mutation
<222> LOCATION: (446)..(446)
<223> OTHER INFORMATION: adenin

<400> SEQUENCE: 5

```
atg cgt gaa cgc atc tcc aac gct aag cga gtg gtg gtg aaa att ggt     48
Met Arg Glu Arg Ile Ser Asn Ala Lys Arg Val Val Val Lys Ile Gly
1               5                   10                  15 tcg tcc tca ttg act aac gat gag gac gga cac acc gtc gat ccc aac     96
Ser Ser Ser Leu Thr Asn Asp Glu Asp Gly His Thr Val Asp Pro Asn
            20                  25                  30
```

```
cgc atc aac act att gtc aat gcc ttg caa gca cgc atg gaa gct ggc       144
Arg Ile Asn Thr Ile Val Asn Ala Leu Gln Ala Arg Met Glu Ala Gly
        35                  40                  45 tcg gac ctc atc gtt gtg tcc tct ggc gca gtg gcc gcg gga atg gcc       192
Ser Asp Leu Ile Val Val Ser Ser Gly Ala Val Ala Ala Gly Met Ala
50                  55                  60 ccg ctt gga ttg agc acc cgg ccc acg gaa ttg gca gtc aag cag gct       240
Pro Leu Gly Leu Ser Thr Arg Pro Thr Glu Leu Ala Val Lys Gln Ala
65                  70                  75                  80 gca gca gca gtg ggg caa gtt cac ctc atg cac cag tgg gga cgt tct       288
Ala Ala Ala Val Gly Gln Val His Leu Met His Gln Trp Gly Arg Ser
                85                  90                  95 ttt gcc cgg tat ggt cgc ccc atc ggc cag gtg ctt ctt acc gca gct       336
Phe Ala Arg Tyr Gly Arg Pro Ile Gly Gln Val Leu Leu Thr Ala Ala
            100                 105                 110 gat gca gga aag cgt gat cgt gcg agg aat gcg cag cgt acc atc gac       384
Asp Ala Gly Lys Arg Asp Arg Ala Arg Asn Ala Gln Arg Thr Ile Asp
            115                 120                 125 aag ctg cgc att ttg ggc gcg gtt cct atc gtc aat gaa aat gac acc       432
Lys Leu Arg Ile Leu Gly Ala Val Pro Ile Val Asn Glu Asn Asp Thr
        130                 135                 140 gtg gca acc acc gat gtg aat ttt ggt gac aac gac cga ctt gct gca       480
Val Ala Thr Thr Asp Val Asn Phe Gly Asp Asn Asp Arg Leu Ala Ala
145                 150                 155                 160 att gtg gcg cac ctg gtg tcg gct gac gct ttg gtg ctg ctc agt gac       528
Ile Val Ala His Leu Val Ser Ala Asp Ala Leu Val Leu Leu Ser Asp
                165                 170                 175 gtg gat gga ctt ttt gat aag aac cct act gat ccc acc gcg aag ttt       576
Val Asp Gly Leu Phe Asp Lys Asn Pro Thr Asp Pro Thr Ala Lys Phe
            180                 185                 190 att tcc gag gtt cgt gac ggc aat gat ttg aaa ggt gtc att gcc ggc       624
Ile Ser Glu Val Arg Asp Gly Asn Asp Leu Lys Gly Val Ile Ala Gly
            195                 200                 205 gac ggc gga aaa gtg ggc acc ggc ggc atg gca tca aag gtg tct gct       672
Asp Gly Gly Lys Val Gly Thr Gly Gly Met Ala Ser Lys Val Ser Ala
210                 215                 220 gca cgt ttg gct tcc cga agt ggc gtg cct gtg ctg ttg acc tct gcg       720
Ala Arg Leu Ala Ser Arg Ser Gly Val Pro Val Leu Leu Thr Ser Ala
225                 230                 235                 240 gca aac att ggc cca gca ctg gaa gac gcc cag gtg ggc act gta ttc       768
Ala Asn Ile Gly Pro Ala Leu Glu Asp Ala Gln Val Gly Thr Val Phe
                245                 250                 255 cac ccc aag gac aac cgc ctc tcc gcg tgg aag ttc tgg gct ttg tat       816
His Pro Lys Asp Asn Arg Leu Ser Ala Trp Lys Phe Trp Ala Leu Tyr
            260                 265                 270 gcc gca gat act gca gga aag atc cga ctt gat gat ggc gcg gtg gaa       864
Ala Ala Asp Thr Ala Gly Lys Ile Arg Leu Asp Asp Gly Ala Val Glu
            275                 280                 285 gca gtg acc tcc ggt ggt aaa tct ttg ctg gct gtg ggc att act gag       912
Ala Val Thr Ser Gly Gly Lys Ser Leu Leu Ala Val Gly Ile Thr Glu
290                 295                 300 atc att ggt gat ttc caa cag ggt gag atc gtg gag atc ttg gga cct       960
Ile Ile Gly Asp Phe Gln Gln Gly Glu Ile Val Glu Ile Leu Gly Pro
305                 310                 315                 320 gcc ggc caa atc atc ggg cga ggc gag gtg tcc tac gat tct gat acc      1008
Ala Gly Gln Ile Ile Gly Arg Gly Glu Val Ser Tyr Asp Ser Asp Thr
                325                 330                 335 ttg caa tca atg gtt ggc atg caa acg cag gac ctt cca gat ggc atg      1056
Leu Gln Ser Met Val Gly Met Gln Thr Gln Asp Leu Pro Asp Gly Met
            340                 345                 350
```

```
cag cgc ccg gta gtg cat gca gat tat ctg tcc aac tac gcc agc cgc    1104
Gln Arg Pro Val Val His Ala Asp Tyr Leu Ser Asn Tyr Ala Ser Arg
        355                 360                 365 gcg taa                                                             1110
Ala
```

<210> SEQ ID NO 6
<211> LENGTH: 369
<212> TYPE: PRT
<213> ORGANISM: Coryneform bacterium

<400> SEQUENCE: 6

```
Met Arg Glu Arg Ile Ser Asn Ala Lys Arg Val Val Lys Ile Gly
1               5                   10                  15

Ser Ser Ser Leu Thr Asn Asp Glu Asp Gly His Thr Val Asp Pro Asn
            20                  25                  30

Arg Ile Asn Thr Ile Val Asn Ala Leu Gln Ala Arg Met Glu Ala Gly
        35                  40                  45

Ser Asp Leu Ile Val Val Ser Ser Gly Ala Val Ala Ala Gly Met Ala
    50                  55                  60

Pro Leu Gly Leu Ser Thr Arg Pro Thr Glu Leu Ala Val Lys Gln Ala
65                  70                  75                  80

Ala Ala Ala Val Gly Gln Val His Leu Met His Gln Trp Gly Arg Ser
                85                  90                  95

Phe Ala Arg Tyr Gly Arg Pro Ile Gly Gln Val Leu Leu Thr Ala Ala
            100                 105                 110

Asp Ala Gly Lys Arg Asp Arg Ala Arg Asn Ala Gln Arg Thr Ile Asp
        115                 120                 125

Lys Leu Arg Ile Leu Gly Ala Val Pro Ile Val Asn Glu Asn Asp Thr
    130                 135                 140

Val Ala Thr Thr Asp Val Asn Phe Gly Asp Asn Asp Arg Leu Ala Ala
145                 150                 155                 160

Ile Val Ala His Leu Val Ser Ala Asp Ala Leu Val Leu Leu Ser Asp
                165                 170                 175

Val Asp Gly Leu Phe Asp Lys Asn Pro Thr Asp Pro Thr Ala Lys Phe
            180                 185                 190

Ile Ser Glu Val Arg Asp Gly Asn Asp Leu Lys Gly Val Ile Ala Gly
        195                 200                 205

Asp Gly Gly Lys Val Gly Thr Gly Gly Met Ala Ser Lys Val Ser Ala
    210                 215                 220

Ala Arg Leu Ala Ser Arg Ser Gly Val Pro Leu Leu Thr Ser Ala
225                 230                 235                 240

Ala Asn Ile Gly Pro Ala Leu Glu Asp Ala Gln Val Gly Thr Val Phe
                245                 250                 255

His Pro Lys Asp Asn Arg Leu Ser Ala Trp Lys Phe Trp Ala Leu Tyr
            260                 265                 270

Ala Ala Asp Thr Ala Gly Lys Ile Arg Leu Asp Asp Gly Ala Val Glu
        275                 280                 285

Ala Val Thr Ser Gly Gly Lys Ser Leu Leu Ala Val Gly Ile Thr Glu
    290                 295                 300

Ile Ile Gly Asp Phe Gln Gln Gly Glu Ile Val Glu Ile Leu Gly Pro
305                 310                 315                 320

Ala Gly Gln Ile Ile Gly Arg Gly Glu Val Ser Tyr Asp Ser Asp Thr
                325                 330                 335

Leu Gln Ser Met Val Gly Met Gln Thr Gln Asp Leu Pro Asp Gly Met
            340                 345                 350
```

```
Gln Arg Pro Val Val His Ala Asp Tyr Leu Ser Asn Tyr Ala Ser Arg
        355                 360                 365
Ala
```

VARIANT POLYNUCLEOTIDE FOR INCREASING L-PROLINE PRODUCTION

The present invention relates to an enzyme having γ-glutamyl kinase activity. More particularly, the present invention characterizes those enzymes which have a proteinogenic amino acid other than glycine at position 149 of the amino acid sequence or a comparable position.

The enzymes having γ-glutamyl kinase activity are preferably employed in the fermentative production of L-proline. The L-proline biosynthetic pathway, starting from glutamate, is depicted in scheme 1.

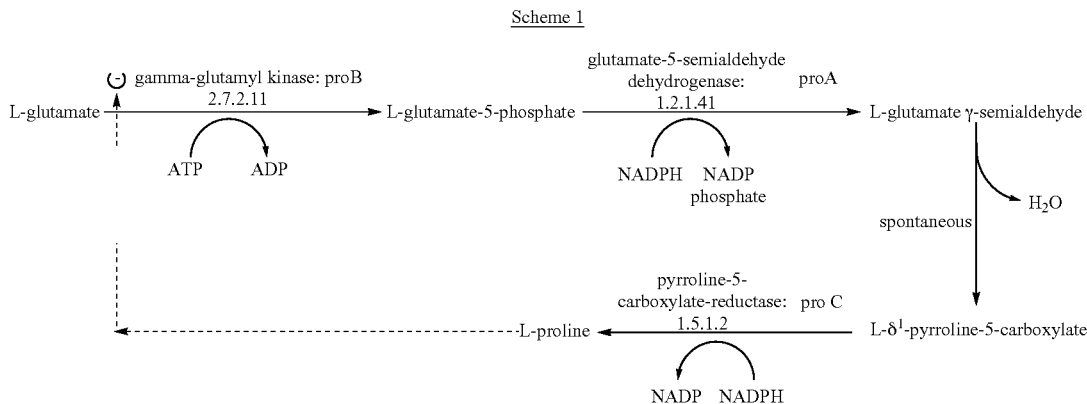

Scheme 1

It is known that amino-acids can be produced by fermenting strains of, for example, coryneform bacteria, in particular *Corynebacterium glutamicum*. Due to the great importance, efforts are continually being made to improve the production processes. Procedural improvements may concern measures relating to fermentation technology, such as, for example, stirring or oxygen supply, or the composition of the nutrient media, such as, for example, sugar concentration during the fermentation, or the working-up to the product form, for example by means of ion exchange chromatography, or the intrinsic performance properties of the microorganism itself.

The performance properties of these microorganisms are improved by applying methods of mutagenesis, selection and mutant choice. This results in strains which are resistant to anti-metabolites or auxotrophic for metabolites important for regulation and produce amino acids. A known anti-metabolite is the proline analogue 3,4-dehydro-DL-proline (DHP).

For some years now, recombinant DNA methods have likewise been used for improving L-amino acid-producing *Corynebacterium* strains by amplifying individual amino acid biosynthesis genes and investigating the effect on amino acid production.

The nucleotide sequence of the *Corynebacterium glutamicum* genome is described, inter alia, in EP-A-1108790 and has also been deposited in the National Center for Biotechnology Information (NCBI) database of the National Library of Medicine (Bethesda, Md., USA) under accession numbers NC_003450.2 and BX927148.1 to BX927157.1.

Sleator et al. report the possibility of causing overproduction in proline biosynthesis by mutating the *Listeria monocytogenes* proB-Gen (Appl. Environ. Microbiol. 2001, 67, 4560-5). The mutations specified therein and referred to as successful concern proB genes coding for γ-glutamyl kinases which have the following mutations: V121I, A144V and E146K. In addition, mention is made of the fact that the regions in which these mutations occur correspond very well to the region also identified in other organisms as a target region for advantageous mutations.

It was therefore the object of the present invention to make available further mutated and, where appropriate, improved protein variants of a γ-glutamyl kinase, which may be employed advantageously in a technical process for fermentative production of L-proline.

This object and other objects which are not specified in detail but which arise in an obvious way from the prior art are achieved by stating the γ-glutamyl kinases of claim 1. Claim 2 focuses on preferred enzymes of this kind. Claim 3 and 4 relates to the nucleotide sequences encoding these enzymes, respectively, while claim 5 focuses on recombinantly produced vehicles having the nucleotide sequences just mentioned. Claim 5, finally, relates to a production process according to the invention for L-proline with the aid of the enzymes mentioned.

By providing a γ-glutamyl kinase (product of the proB gene) which has a proteinogenic amino acid other than glycine at amino acid position 149 or a comparable position, the object set out is achieved particularly surprisingly, albeit no less advantageously. Compared to the wild-type enzymes, γ-glutamyl kinases having an appropriate mutation assist in producing L-proline in an improved manner in a fermentative production process. Using the methods according to the invention, it is possible to improve the performance of the host organisms or of the fermentation process with respect to one or more of the parameters selected from the group of product concentration (product per volume), product yield (product formed per carbon source consumed) and product formation (product formed per volume and time) or else other process parameters and combinations thereof by at least 0.5%, at least 1%, at least 1.5% or at least 2%, based on the starting strain or parent strain or the fermentation process with the use of said enzymes.

Preference is given to providing γ-glutamyl kinases in which an amino acid, preferably L-amino acid, selected from the group consisting of Lys, Asn, Arg, Ser, Thr, Ile, Met, Glu, Asp, Ala, Val, Gln, His, Pro, Leu, Tyr, Trp, Cys or Phe is present at the amino acid position as defined according to the invention or a comparable position. (The amino acids mentioned, including glycine, are also referred to as proteinogenic amino acids in the art.) Very particular preference is given to the substitution of glycine with L-aspartic acid at position 149 (G149D) in the said enzyme. Most preference is given to a γ-glutamyl kinase according to the invention, as specified above, which is 369±40, preferably ±20, more preferably ±10 and very particularly preferably +5 amino acids or ±3 amino acids in length. Enzymes intrinsic to the host, called aminopeptidases, are known to be able to cleave the N-terminal amino acid methionine off the protein formed. It is furthermore known that cleaving off one (1) or two (2) and no more than three (3) amino acids from the C terminus of the protein impairs the enzyme activity only negligibly at most, if at all. However, the enzyme may increase in length due to appending certain fusion proteins (see below).

The present invention also encompasses the amino acid sequence of SEQ ID NO.: 2, preferably 4, or a sequence which is at least 90% identical thereto, with the sequences comprising the amino acid substitution of glycine by another amino acid, in particular any of the preferred amino acids stated, at position 149 or a comparable position. The invention thus also encompasses those enzymes which have the abovementioned degrees of identity at the amino acid level in comparison with SEQ ID NO.: 2, preferably 4. These enzymes may likewise originate from natural sources. Alternatively, they may have been modified by recombinant DNA technology in such a way that the skilled worker may predict the enzymatic activity to be retained or essentially retained (cf. for example Sambrook et al, "Molecular Cloning, A Laboratory Handbook", 2nd edition 1989, CSH Press, Cold Spring Harbor, Ausubel et al. "Current Protocols in Molecular Biology", John Wiley & Sons, NY 2001). Thus, amino acids which are not present at the active site and whose substitution by an amino acid "of the same kind" is, prima facie, not expected to result in a substantially altered three-dimensional structure may be substituted by an amino acid "of the same kind". It may be expected, for example, that certain amino acids with non-polar side chains (amino acids of the same kind) can be substituted, e.g. isoleucine by valine, without this having a (substantial) influence on the biological or enzymic function of the enzyme according to the invention, or on the enzymic activity. The skilled worker may, on the basis of his knowledge, reach corresponding conclusions also for the substitution of other types of amino acids (for example the replacement of basic amino acids with other basic amino acids or of amino acids with uncharged polar side chains with other amino acids from this group).

Preference is likewise given to a γ-glutamyl kinase having at least the amino acid sequence corresponding to positions, or comparable positions, 145 to 154, more preferably 130 to 169 and very particularly preferably 110 to 189 of SEQ. ID NO.: 2, preferably 4, it being possible for the length of the γ-glutamyl kinase amino acid sequence to correspond to the numbers indicated above.

In a furthermore preferred embodiment, the enzymes according to the invention additionally comprise at least one heterologous amino acid section by which these polypeptides are characterized as fusion proteins. Examples of heterologous components of the fusion protein according to the invention may be tags (e.g. His tag or Flag tag) which may be employed in the purification of the fusion proteins according to the invention. In other embodiments, the heterologous components may have a separate enzymic activity. In such a case, the two enzymic components are preferably connected by a linker, such as a flexible glycine or glycine-serine linker of 6-10 amino acids in length, in order to ensure functionality of the components. The term "heterologous", as used herein, may mean, on the one hand, that the components of the fusion protein do not naturally occur together in a covalently linked form and, on the other hand, that the components are derived from different species. Fusion proteins are usually prepared by means of recombinant DNA technology (see Sambrook et al., loc. cit.).

In a further embodiment, the present invention relates to a nucleotide sequence (nucleic acid sequence) encoding a γ glutamyl kinase according to the invention, as specified above. Accordingly, the invention also relates to replicable nucleotide sequences coding for the enzyme γ-glutamyl kinase, it being possible for the corresponding amino acid sequences encoded by these nucleotide sequences to have any proteinogenic amino acid, except glycine, at position 149 or a comparable position.

The nucleotide sequences of the invention preferably encode a γ-glutamyl kinase, with the corresponding, encoded amino acid sequence comprising an amino acid selected from the group consisting of Lys, Asn, Arg, Ser, Thr, Ile, Met, Glu, Asp, Ala, Val, Gln, His, Pro, Leu, Tyr, Trp, Cys or Phe at position 149 or a comparable position. A nucleotide sequence encoding a γ-glutamyl kinase which has an L-aspartic acid at position 149 or a comparable position is very particularly preferred.

The invention likewise relates to replicable nucleic acid sequences encoding a γ-glutamyl kinase which has the amino acid substitution according to the invention at position 149 or a comparable position, with these sequences
a) being at least 70% identical to Seq. ID NO.: 1, preferably SEQ. ID NO.: 3, or
b) encoding a γ-glutamyl kinase according to the invention, which is 369±40 amino acids in length, or
c) encoding a γ-glutamyl kinase according to the invention, which has the amino acid sequence of SEQ. ID No.: 2, preferably SEQ. ID NO.: 4, at least in positions or comparable positions 145 to 154, or
d) encoding a γ-glutamyl kinase according to the invention, which has the amino acid sequence of SEQ. ID No.: 2, preferably SEQ. ID NO.: 4, at least in positions or comparable positions 145 to 154 and hybridizes under stringent experimental conditions to the nucleotide sequence complementary to SEQ. ID NO.: 1 or SEQ. ID NO.: 3, or
f) replicable nucleotide sequence which encodes the enzyme according to the invention, γ-glutamyl kinase, and whose base sequence comprises adenine at position 446, as depicted in SEQ ID NO.: 3.

The scope of the claims preferably likewise comprises replicable nucleic acid sequences encoding γ-glutamyl kinases according to the invention, which are 369±20, more preferably ±10 and most preferably ±5 or ±3, amino acid residues in length.

The invention also relates to a nucleotide sequence as depicted in SEQ. ID NO.: 1, preferably 3. As already mentioned, the invention also encompasses those sequences which are at least 70% identical to that sequence at the nucleotide level. An example of a nucleotide sequence which is at least 70% identical to that of SEQ ID NO.: 3 is shown in SEQ ID NO.: 5. SEQ ID NO.:6 shows the amino acid sequence of γ-glutamyl kinase, encoded by SEQ ID NO.: 5.

The invention likewise relates to replicable nucleic acid sequences encoding γ-glutamyl kinases which preferably include at least the amino acid sequence corresponding to positions 130-169 or comparable positions, and very particularly preferably positions 110 to 189 of SEQ ID NO: 2, preferably 4, and which hybridize under stringent experimental conditions with the nucleotide sequence complementary to SEQ ID NO: 1 or SEQ ID NO.: 3.

The term "complementary" means according to the invention that the complementarity extends without gaps across the entire region of the nucleic acid molecule according to the invention. In other words, according to the invention, preference is given to complementarity extending 100% across the entire region of the sequence according to the invention, i.e. from the 5' terminus depicted to the 3' terminus depicted, in particular the coding region (cds). In further preferred embodiments, complementarity extends across a region of at least 19, preferably at least 21, successive nucleotides which preferably do not encode the active site of enzymic activity.

Preference is given to those nucleic acid sequences derived from coryneform bacteria, preferably *Corynebacterium glutamicum*. Nucleic acid sequences of genes or alleles, which are present in the population of a species, are also referred to as endogenous genes or alleles in the art.

The present invention further relates to recombinant (rec) vehicles having the nucleotide sequences according to the invention. Suitable vehicles are any embodiments considered for this purpose by the skilled worker, in particular vectors and host organisms.

Examples of host organisms which may be mentioned in this regard are yeasts such as *Hansenula polymorpha, Pichia* sp., *Saccharomyces cerevisiae*, prokaryotes such as *E. coli, Bacillus subtilis*, coryneform bacteria such as *Corynebacterium glutamicum*, or eukaryotes such as mammalian cells, insect cells or plant cells. These organisms accumulate, where appropriate already prior to the measures of the present invention, L-proline in their cells or in the fermentation medium surrounding them. Thus, in this preferred embodiment, the host according to the invention is a recombinant cell which has been transformed or transfected with a nucleic acid sequence according to the invention or a vector according to the invention (see below) or provided with them by way of conjugation (the terms "transformation", "transfection" and "conjugation" are used synonymously according to the present invention). Transformation and transfection, respectively, may be carried out according to known methods, for example by means of calcium phosphate co-precipitation, lipofection, electroporation, particle bombardment or viral infection. The cell according to the invention may contain the recombinant nucleic acid extrachromosomally or in a chromosomally integrated form. In other words, the transfection/transformation may be a stable or a transient one. The processes for cloning are well known to the skilled worker (Sambrook, J.; Fritsch, E. F. and Maniatis, T. (1989), Molecular cloning: a laboratory manual, $2^{nd}$ ed., Cold Spring Harbor Laboratory Press, New York). *E. coli* strains may be utilised for the recombinant preparation and mutagenesis methods, which include inter alia: *E. coli* XL1 Blue, NM 522, JM101, JM109, JM105, RR1, DH5α, TOP10, HB101, BL21 codon plus, BL21 (DE3) codon plus, BL21, BL21 (DE3), MM294. Plasmids used inter alia for cloning the gene construct having the nucleic acid according to the invention into the host organism are likewise known to the skilled worker (see also PCT/EP03/07148; see below). A host of the genus *Corynebacterium*, of which particular mention may be made, is the species *Corynebacterium glutamicum* which is known in the art. Examples of known wild-type strains of the genus *Corynebacterium* are:

*Corynebacterium glutamicum* ATCC13032
*Corynebacterium acetoglutamicum* ATCC15806
*Corynebacterium acetoacidophilum*. ATCC13870
*Corynebacterium effiziens* DSM 44549
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020.

Information regarding the taxonomic classification of strains of this group of bacteria can be found, inter alia, in Kämpfer and Kroppenstedt (Canadian Journal of Microbiology 42, 989-1005 (1996)) and in U.S. Pat. No. 5,250,434. For some years now (Liebl et al., International Journal of Systematic Bacteriology 41(2), 255-260 (1991)), coryneform bacteria with the species names "*Brevibacterium flavum*", "*Brevibacterium lactofermentum*" und "*Brevibacterium divaricatum*" have been classified under the species *Corynebacterium glutamicum*. Coryneform bacteria with the species name "*Corynebacterium melassecola*" likewise belong to the species *Corynebacterium glutamicum*.

Examples of L-proline-producing strains of coryneform bacteria are the strains:
*Brevibacterium lactofermentum* NRRL B-11421,
*Brevibacterium flavum* NRRL B-11422,
*Corynebacterium glutamicum* NRRL B-11423,
*Microbacterium ammoniaphilum* NRRL B-11424,
*Corynebacterium glutamicum* ATCC 21157,
*Corynebacterium glutamicum* ATCC 21158,
*Corynebacterium glutamicum* ATCC 21159,
*Corynebacterium glutamicum* ATCC 21355,
*Corynebacterium acetophilum* FERM-P 4045,
*Corynebacterium acetoacidophilum* FERM-P 4962,
*Arthrobacter citreus* FERM-P 4963, and
*Microbacterium ammoniaphilum* FERM-P 4964,
all of which are described in U.S. Pat. No. 4,224,409 and U.S. Pat. No. 4,444,885.

In the vectors according to the invention, the nucleic acid sequences according to the invention are preferably operatively linked to an expression control sequence so as to be able to be transcribed and, where appropriate, translated in a suitable host cell. Expression control sequences usually comprise a promoter and, where appropriate, further regulatory sequences such as operators or enhancers. It is furthermore also possible for translation initiation sequences to be present. Suitable expression control sequences for prokaryotic or eukaryotic host cells are known to the skilled worker (see, for example, Sambrook et al., loc. cit.). The recombinant vector according to the invention may furthermore also include usual elements such as an origin of replication and a selection marker gene. Examples of suitable recombinant vectors are plasmids, cosmids, phages, or viruses (see, for example, Sambrook et al., supra).

Suitable plasmids are in principle any embodiments available for this purpose to the skilled worker. Such plasmids may be found, for example, in the paper by Studier and co-workers (Studier, W. F.; Rosenberg A. H.; Dunn J. J.; Dubendroff J. W.; (1990), Use of the T7 RNA polymerase to direct expression of cloned genes, Methods Enzymol. 185, 61-89) or in the brochures from Novagen, Promega, New England Biolabs, Clontech or Gibco BRL. Further preferred plasmids and vectors may be found in: Glover, D. M. (1985), DNA cloning: a practical approach, Vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

Plasmids which may be used for cloning the gene constructs having the contemplated nucleic acid sequences into the host organism in a very particularly preferred manner are or are based on: pUC18/19 (Roche Biochemicals), pKK-177-3H (Roche Biochemicals), pBTac2 (Roche Biochemicals), pCR (Invitrogen), pKK223-3 (Amersham Pharmacia Biotech), pKK-233-3 (Stratagene) or pET (Novagen). Other preferred plasmids are pBR322 (DSM3879), pACYC184 (DSM4439) and pSC101 (DSM6202), all of which may be obtained from the DSMZ-Deutsche Sammlung von Mikroorganismen und Zellkulturen GmbH, Brunswick, Germany. Examples of preferred promoters are the T7 promoter, lac promoter, tac promoter, trp promoter, rha promoter and ara promoter.

Preferably, the γ-glutamyl kinases according to the invention or the nucleic acids encoding them are overexpressed in coryneform bacteria, preferably of the genus *Corynebacterium*, particularly preferably of the species *Corynebacterium glutamicum*.

Overexpression means an increase in the intracellular concentration or activity of the γ-glutamyl kinases according to the invention.

The overexpression measures increase the activity or concentration of the corresponding protein usually by at least 10%, 25%, 50%, 75%, 100%, 150%, 200%, 300%, 400% or 500%, up to a maximum of 1000% or 2000%, based on the activity or concentration of the protein in the starting microorganism.

Overexpression may be achieved by increasing the copy number of the genes or alleles according to the invention by at least one (1) copy or by mutating the promoter region and regulatory region or the ribosome-binding site which is located upstream of the structural gene. Expression cassettes incorporated upstream of the structural gene act in the same manner. In addition, inducible promoters make it possible to increase expression during fermentative L-proline production. Measures of extending the mRNA life-time likewise improve expression. The enzyme activity is furthermore amplified by preventing degradation of the enzyme protein. The genes or gene constructs may be present either in plasmids with different copy numbers or in the chromosome in an integrated and amplified form. Alternatively, the genes in question may furthermore be overexpressed by altering the media composition and the culturing process.

Plasmids which are replicated in coryneform bacteria are useful for increasing the copy number of the proB alleles according to the invention. Numerous known plasmid vectors such as, for example, pZ1 (Menkel et al., Applied and Environmental Microbiology (1989) 64: 549-554), PEKEx1 (Eikmanns et al., Gene 102:93-98 (1991)) or pHS2-1 (Sonnen et al., Gene 107:69-74 (1991)) are based on the cryptic plasmids pHM1519, pBL1 or pGA1. Other plasmid vectors such as, for example, those based on pCG4 (U.S. Pat. No. 4,489,160), or pNG2 (Serwold-Davis et al., FEMS Microbiology Letters 66, 119-124 (1990)) or pAG1 (U.S. Pat. No. 5,158,891) may be used in the same manner. An overview over *Corynebacterium glutamicum* plasmid vectors can be found in Tauch et al. (Journal of Biotechnology 104(1-3), 27-40 (2003).

It is furthermore possible to increase the copy number by applying the method of chromosomal gene amplification which has been described, for example, by Reinscheid et al. (Applied and Environmental Microbiology 60, 126-132 (1994)) in the context of duplication and amplification of the hom-thrB-operon. This method involves cloning the complete gene or allele into a plasmid vector which can be replicated in a host (typically *E. coli*) but not in *C. glutamicum*. Examples of suitable vectors are pSUP301 (Simon et al., Bio/Technology 1, 784-791 (1983)), pK18mob or pK19mob (Schäfer et al., Gene 145, 69-73 (1994)), pGEM-T (Promega Corporation, Madison, Wis., USA), pCR2.1-TOPO (Shuman, Journal of Biological Chemistry 269:32678-84 (1994); U.S. Pat. No. 5,487,993), pCR®Blunt (Firma Invitrogen, Groningen, the Netherlands; Bernard et al., Journal of Molecular Biology, 234: 534-541 (1993)), pEM1 (Schrumpf et al., Journal of Bacteriology 173:4510-4516 (1991)) or pBGS8 (Spratt et al., Gene 41: 337-342 (1986)). The plasmid vector containing the gene or allele to be amplified is subsequently transferred by means of conjugation or transformation to the desired *C. glutamicum* strain. The method of conjugation is described in Schäfer et al. (Applied and Environmental Microbiology 60, 756-759 (1994)), for example. Transformation methods are described in Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)), for example. After homologous recombination by way of a "cross over" event, the resulting strain contains at least two copies of the gene or allele in question. In order to increase the copy number by at least 1, 2 or 3, it is in particular also possible to use the tandem-amplification method as described in WO 03/014330 or the method of amplification by way of integration at a desired location, as described in WO 03/040373.

Mutagenesis methods described in the prior art are used for generating the amino acid substitution according to the invention in γ-glutamyl kinases (e.g. SEQ ID NO: 2) and other proB mutations according to the invention, characterized by an amino acid substitution at position 149. Suitable mutagenesis methods are any methods available for this purpose to the skilled worker.

Classical in-vivo mutagenesis methods using mutagenic substances such as, for example, N-methyl-N'-nitro-N-nitrosoguanidine (MNNG) or ultraviolet light may be used for mutagenesis. The mutagenized cells are, where appropriate, subsequently applied to a minimal agar containing 3,4-dehydro-DL-proline at concentrations of approx. 0.5-1 g/l, approx. 1-2 g/l or approx. 2-3 g/l. Individual mutants are isolated and the nucleotide sequence of the proB gene or allele is determined, where appropriate after a previous cloning process. It is furthermore possible to use for the mutagenesis in-vitro methods such as, for example, treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger [genetic engineering for beginners], Spektrum Akademischer Verlag, Heidelberg, 1993; textbook by Knippers ("Molekulare Genetik" [molecular genetics], 6th edition, Georg Thieme Verlag, Stuttgart, Germany, 1995); Winnacker ("Gene und Klone" [genes and clones], VCH Verlagsgesellschaft, Weinheim, Germany, 1990); Hagemann ("Allgemeine Genetik" [general genetics], Gustav Fischer Verlag, Stuttgart, Germany, 1986)) or the polymerase chain reaction (PCR) as described in the manual by Newton and Graham (PCR, Spektrum Akademischer Verlag, Heidelberg, Germany, 1994). They include, in particular, saturation mutagenesis, random mutagenesis, in-vitro recombination methods and site-directed mutagenesis (Eigen, M. and Gardiner, W. (1984), Evolutionary molecular engineering based on RNA replication, Pure Appl. Chem. 56, 967-978; Chen, K. and Arnold, F. (1991), Enzyme engineering for nonaqueous solvents: random mutagenesis to enhance activity of subtilisin E in polar organic media. Bio/Technology 9, 1073-1077; Horwitz, M. and Loeb, L. (1986), Promoters Selected From Random DNA-Sequences, Proc Natl Acad Sci USA 83, 7405-7409; Dube, D. and L. Loeb (1989), Mutants Generated By The Insertion Of Random Oligonucleotides Into The Active-Site Of The Beta-Lactamase Gene, Biochemistry 28, 5703-5707; Stemmer, P. C. (1994), Rapid evolution of a protein in vitro by DNA shuffling, Nature 370, 389-391 and Stemmer, P. C. (1994), DNA shuffling by random fragmentation and reassembly: In vitro recombination for molecular evolution. Proc Natl Acad Sci USA 91, 10747-10751). The use of in-vitro methods involves amplifying the proB gene described in the prior art with the aid of the polymerase chain reaction, starting from total DNA isolated from a wild-type strain, cloning the said gene, where appropriate, into suitable plasmid vectors and then subjecting the DNA to the mutagenesis process. Instructions on the amplification of DNA sequences with the aid of the polymerase chain reaction (PCR) can be found by the skilled worker, inter alia, in the manual by Gait: oligonucleotide Synthesis: A Practical Approach (IRL Press, Oxford, UK, 1984) and in Newton and Graham: PCR (Spektrum Akademischer Verlag, Heidelberg, Germany, 1994). In the same way it is also possible to use methods of in-vitro mutagenesis, as described, for example, in the well-known manual by Sambrook et al. (Molecular Cloning, A Laboratory Manual, 2nd ed., Cold Spring Harbor Laboratory Press, Cold Spring Harbor, N.Y., USA, 1989). Corresponding methods are also commercially available in the form of "kits" such as, for example, the "QuikChange Site-Directed Mutagenesis Kit" from Stratagene (La Jolla, USA), described by Papworth et al. (Strategies 9(3), 3-4 (1996)). Suitable proB mutants are subsequently selected and investigated by the methods described above.

For production of L-proline, it may be advantageous, in addition to using the γ-glutamyl kinases according to the invention, which may or may not have been overexpressed or amplified, to amplify, in particular to overexpress, besides the said kinases, at the same time one or more enzymes of proline biosynthesis. Preference is usually given to using endogenous genes.

"Endogenous genes" or "endogenous nucleotide sequences" means the genes or nucleotide sequences and alleles present in the population of a species.

In this context, the term amplification describes the increase in the intracellular activity or concentration of one or more enzymes or proteins in a microorganism, which are encoded by the corresponding DNA, by, for example, increasing the copy number of the gene or genes, using a strong promoter or using a gene or allele which encodes a corresponding enzyme or protein with high activity and, where appropriate, combining these measures.

The amplification, in particular overexpression, measures increase the activity or concentration of the corresponding enzyme or protein usually by at least 10%, 25%, 50%, 75%, 100%, 150%, 200%, 300%, 400% or 500%, up to a maximum of 1000% or 2000%, based on that of the wild-type protein or on the activity or concentration of the protein in the starting microorganism.

For producing L-proline it is thus possible, in addition to using the variant of the proB gene according to the invention, to amplify, in particular overexpress, one or more of the genes selected from the group consisting of
the gdh gene coding for glutamate dehydrogenase (EC 1.4.1.4),
the proA gene coding for γ-glutamyl-phosphate reductase (EC 1.2.1.41),
the proC gene coding for pyrroline-5-carboxylate reductase (EC 1.5.1.2), and
the ocd gene coding for ornithine cyclodeaminase (EC 4.3.1.12).

For production of L-proline it may furthermore be advantageous, in addition to using mutants according to the invention of the proB gene, at the same time to attenuate, in particular reduce expression of, one or more of the endogenous genes selected from the group consisting of
the ilvA gene coding for threonine deaminase (EC 4.2.1.16),
the putA gene coding for proline dehydrogenase/pyrroline-5-carboxylate dehydrogenase (EC 1.5.99.8),
the sucA gene coding for 2-ketoglutarate dehydrogenase (EC 1.2.4.2),
the sucB gene coding for dihydrolipoamide succinyltransferase (EC 2.3.1.61), and
the argD gene coding for acetylornithine aminotransferase (EC 2.6.1.11).

In this connection, the term "attenuation" describes the reduction or elimination of the intracellular activity or concentration of one or more enzymes or proteins which are encoded by the corresponding DNA in a microorganism by, for example, using a weak promoter or using a gene or allele which encodes a corresponding enzyme with low activity or inactivating the corresponding gene or enzyme or protein and, where appropriate, combining these measures.

Attenuation may be achieved by reducing or eliminating either expression of the genes or the catalytic or regulatory properties of the enzyme proteins. Both measures may be combined, where appropriate.

Gene expression may be reduced by a suitable culturing process or by genetic modification (mutation) of the signal structures of gene expression. Examples of signal structures of gene expression are repressor genes, activator genes, operators, promoters, attenuators, ribosome-binding sites, the start codon and terminators. Information on this can be found by the skilled worker, for example, in the patent application WO 96/15246, in Boyd and Murphy (Journal of Bacteriology 170: 5949-5952 (1988)), in Voskuil and Chambliss (Nucleic Acids Research 26: 3584-3590 (1998), in Pátek et al. (Microbiology 142: 1297-309 (1996) and Journal of Biotechnology 104: 311-323 (2003)) and in known textbooks of genetics and molecular biology such as, for example, the textbook by Knippers ("Molekulare Genetik", $6^{th}$ edition, Auflage, Georg Thieme Verlag, Stuttgart, Germany, 1995) or that by Winnacker ("Gene und Klone", VCH Verlagsgesellschaft, Weinheim, Germany, 1990).

An example of specific regulation of gene expression is the cloning of the gene to be attenuated to come under the control of a promoter inducible by adding metered amounts of IPTG (isopropyl-β-D-thiogalactopyranoside), such as, for example, the trc promoter or the tac promoter. Useful vectors here are, for example, the *Escherichia coli* expression vector pXK99E (WO0226787; deposited in accordance with the Budapest Treaty on 31 Jul. 2001 in DH5alpha/pXK99E as DSM14440 with the Deutsche Sammlung für Mikroorganismen und Zellkulturen (DSMZ, Brunswick, Germany)) or pVWEx2 (Wendisch, Ph. D. thesis, Berichte des Forschungszentrums Jülich, Jül-3397, ISSN 0994-2952, Jülich, Germany (1997)), which enable the cloned gene to be expressed in an IPTG-dependent manner in *Corynebacterium glutamicum*.

This method was employed, for example, in the patent WO02/26787 for regulated expression of the deaD gene by integrating the vector pXK99EdeaD into the *Corynebacterium glutamicum* genome, and by Simic et al. (Applied and Environmental Microbiology 68: 3321-3327 (2002)) for regulated expression of the glyA gene by integration of the vector pK18mobglyA' in *Corynebacterium glutamicum*.

Another method of specifically reducing gene expression is the antisense technique which involves introducing into the target cells short oligoribonucleotides or oligodeoxyribonucleotides or vectors for synthesizing longer antisense RNA. There, the antisense RNA may bind to complementary sections of specific mRNAs and reduce their stability or block translatability. An example of this can be found by the skilled worker in Srivastava et al. (Applied Environmental Microbiology 2000 October; 66 (10): 4366-4371).

Mutations which result in a change or reduction in the catalytic properties of enzyme proteins are known from the prior art; examples which may be mentioned are the studies by Qiu and Goodman (Journal of Biological Chemistry 272: 8611-8617 (1997)), Sugimoto et al. (Bioscience Biotechnology and Biochemistry 61: 1760-1762 (1997)) and Möckel (Ph. D. thesis, Berichte des Forschungszentrums Jülich, Jül-2906, ISSN09442952, Jülich, Germany (1994)). Overviews can be found in known textbooks of genetics and molecular biology, for example that by Hagemann ("Allgemeine Genetik", Gustav Fischer Verlag, Stuttgart, Germany, 1986).

Mutations which come into consideration are transitions, transversions, insertions and deletions. Depending on the effect of the amino acid substitution on the enzyme activity, reference is made to missense mutations or nonsense mutations. A nonsense mutation leads to at least one stop codon being located in the coding region of the gene and consequently to translation being terminated prematurely. Insertions or deletions of at least one base pair in a gene lead to frame shift mutations as a result of which incorrect amino acids are incorporated or translation is terminated prematurely. Deletions of one or more codons typically lead to a total loss of enzyme activity. Instructions for generating such mutations belong to the prior art and can be found in known textbooks of genetics and molecular biology such as the textbook by Knippers ("Molekulare Genetik", 6$^{th}$ edition, Georg Thieme Verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986).

As a result of using the measures for achieving attenuation, the activity or concentration of the corresponding protein is usually lowered to from 0 to 75%, from 0 to 50%, from 0 to 25%, from 0 to 10%, from 0 to 5% or from 0 to 1%, of the activity or concentration of the wild-type protein or of the activity or concentration of the protein in the starting microorganism.

The microorganisms prepared according to the invention, which are likewise a subject-matter of the present invention, may be cultured continuously or discontinuously, in a batch process or a fed-batch process or a repeated fed-batch process, for the purpose of producing L-proline. An overview of known culturing methods is described in the textbook by Chmiel (Bioprozesstechnik 1. Einführung in die Bioverfahrenstechnik [Bioprocess Technology 1. Introduction to Bioprocess Technology] (Gustav Fischer Verlag, Stuttgart, 1991)) or in the textbook by Storhas (Bioreaktoren und periphere Einrichtungen [Bioreactors and Peripheral Equipment] (Vieweg Verlag, Brunswick/Wiesbaden, 1994)).

The culture medium to be used must suitably satisfy the requirements of the particular strains. Descriptions of media for culturing various microorganisms are given in the manual "Manual of Methods for General Bacteriology" published by the American Society for Bacteriology (Washington D.C., USA, 1981).

The carbon source employed may be sugars and carbohydrates, such as, for example, glucose, sucrose, lactose, fructose, maltose, molasses, starch and cellulose, oils and fats, such as, for example, soybean oil, sunflower oil, peanut oil and coconut oil, fatty acids such as, for example, palmitic acid, stearic acid and linoleic acid, alcohols such as, for example, glycerol and ethanol, sugar alcohols such as, for example, ribitol or mannitol and organic acids such as, for example, acetic acid. These substances may be used individually or as mixtures.

The nitrogen source employed may be organic nitrogen-containing compounds such as peptones, yeast extract, meat extract, malt extract, cornsteep liquor, soybean flour and urea, or inorganic compounds such as ammonium sulphate, ammonium chloride, ammonium phosphate, ammonium carbonate and ammonium nitrate. The nitrogen sources may be used individually or as mixtures.

The phosphorus source employed may be phosphoric acid, potassium dihydrogen phosphate or dipotassium hydrogen phosphate or the corresponding sodium-containing salts. The culture medium must furthermore contain salts of metals, for example magnesium sulphate or iron sulphate, which are necessary for growth. Finally, essential growth substances such as amino acids and vitamins may be used in addition to the abovementioned substances. In addition to this, suitable precursors may be added to the culture medium. The added substances mentioned may be added to the culture in the form of a once-only mixture or fed in a suitable manner during the culture.

Basic compounds such as sodium hydroxide, potassium hydroxide, ammonia or aqueous ammonia, or acidic compounds such as phosphoric acid or sulphuric acid are employed in a suitable manner for controlling the pH of the culture. It is possible to use antifoams such as, for example, fatty acid polyglycol esters, for controlling foam formation. Suitable substances which act selectively, such as antibiotics, for example, may be added to the medium in order to maintain the stability of plasmids. In order to maintain aerobic conditions, oxygen or oxygen-containing gas mixtures such as air, for example, are passed into the culture. The temperature of the culture is normally from 20° C. to 45° C., and preferably from 25° C. to 40° C. The culture is continued until a maximum of L-proline has been formed or until the yield or productivity has reached a desired optimal level. This objective is normally achieved within from 10 hours to 160 hours.

Methods for determining L-proline are disclosed in the prior art. The analysis may, for example, take place by means of anion exchange chromatography, followed by ninhydrin derivatization and detection at an appropriate wavelength, as described in Spackman et al. (Analytical Chemistry, 30 (1958), 1190).

Accordingly, another embodiment of the present invention constitutes a process for producing L-proline by
a) fermenting host organisms which express or overexpress at least one of the nucleotide sequences according to the invention and
b) isolating or collecting L-proline, where appropriate with components from the fermentation broth and/or the biomass.

Preference is given to employing a process for producing L-proline, which comprises the following steps:
a) fermenting coryneform bacteria which express or overexpress at least one of the nucleotide sequences according to the invention,
b) concentrating L-proline in the fermentation broth or in the cells of the coryneform bacteria,
c) isolating or collecting L-proline from the fermentation broth, where appropriate
d) with components from the fermentation broth and/or the biomass (from >0 to <100% by weight of biomass, preferably from 10 to 80% by weight, more preferably 20-60% by weight).

The L-proline produced in this way may be collected and isolated and, where appropriate, purified, as determined by the skilled worker.

The process according to the invention is used for fermentative production of L-proline.

The term "comparable position" means according to the invention a position which, by comparing the starting sequence with the comparative sequence with application of a sequence comparison program (BLAST, Altschul et al. J. Mol. Biol. 1990, 215, 403-10) at the comtemplated position of the starting sequence, provides an amino acid position in the comparative sequence which differs from the position to be compared by no more than ±5, more preferably ±4, further preferably ±3, still further preferably ±2, most preferably ±1, and especially zero, positions.

Instructions regarding hybridization can be found by the skilled worker inter alia in the manual "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization is carried out under stringent conditions, i.e. only hybrids in which the probe, for example the nucleotide sequence complementary to SEQ ID NO: 3, and the target sequence, i.e. the polynucleotides treated with the probe, are at least 70% identical, are formed. The stringency of the hybridization, including that of the washing steps, is known to be influenced or determined by varying the buffer composition, the temperature and the salt concentration. The hybridization reaction is generally carried out at relatively low stringency compared to the washing steps (Hybaid Hybridisation Guide, Hybaid Limited, Teddington, UK, 1996).

For example, a buffer corresponding to 5×SSC buffer at a temperature of approx. 50° C.-68° C. may be used for the hybridization reaction. In this case, probes may also hybridize with polynucleotides which are less than 70% identical to the sequence of the probe. Such hybrids are less stable and are removed by washing under stringent conditions. This may be achieved, for example, by lowering the salt concentration to 2×SSC and, where appropriate, subsequently to 0.5×SSC (The DIG System User's Guide for Filter Hybridisation, Boehringer Mannheim, Mannheim, Germany, 1995), with the temperature being set to approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Preference is given to carrying out the washing steps at temperatures of approx. 62° C.-68° C., particularly preferably approx. 64° C.-68° C. or approx. 66° C.-68° C. It is possible, where appropriate, to lower the salt concentration down to a concentration corresponding to 0.2×SSC or 0.1×SSC. By gradually increasing the hybridization temperature in steps of approx. 1-2° C. from 50° C. to 68° C., it is possible to isolate polynucleotide fragments which have at least 70% or at least 80% or at least 90% to 95% or at least 96% to 98% or at least 99% identity to the sequence of the probe employed. Further instructions regarding hybridization are commercially available in the form of "kits" (e.g. DIG Easy Hyb from Roche Diagnostics GmbH, Mannheim, Germany, Catalogue No. 1603558)).

According to the invention, the claimed polypeptides (amino acid sequences) and the nucleic acid sequences also comprise those sequences which have a homology (at the amino acid level) and, respectively, identity (at the nucleic acid level, excluding natural degeneracy) of more than 70%, preferably 80%, more preferably 85% (with respect to the nucleic acid sequence) or 90% (also with respect to the polypeptides), preferably more than 91%, 92%, 93% or 94%, more preferably more than 95% or 96% and particularly preferably more than 97%, 98% or 99% (with respect to both types of sequences) to any of these sequences, as long as the action or purpose of such a sequence is retained. The term "homology" (or identity), as used herein, can be defined by the equation $H(\%)=[1-V/X]\times 100$, where H is homology, X is the total number of nucleobases/amino acids of the comparative sequence and V is the number of different nucleobases/amino acids of the sequence to be considered, based on the comparative sequence. In any case, the term nucleic acid sequences coding for polypeptides includes any sequences that seem possible in accordance with the degeneracy of the genetic code.

The percentage identity to the amino acid sequences indicated in the present specification by SEQ ID numbers may readily be determined by the skilled worker using methods known in the prior art. A suitable program which may be employed according to the invention is BLASTP (Altschul et al., 1997. Gapped BLAST and PSI-BLAST: a new generation of protein database search programs. Nucleic Acids Res: 25(17):3389-3402.). The nucleic acid sequence according to the invention may be a DNA molecule or an RNA molecule. Preference is given to the nucleic acid sequence being a DNA molecule or an mRNA molecule. According to the invention, the DNA molecule may furthermore be a genomic or an isolated DNA molecule. The invention further encompasses embodiments in which the DNA molecule is a PNA molecule or another derivative of a DNA molecule.

The microorganisms mentioned in this application, which are indicated by a DSMZ number, may be obtained from the Deutsche Sammlung für Mikroorganismen und Zellkulturen, Mascheroder Weg 4, Brunswick (Germany).

The invention claimed is:

1. An isolated polynucleotide, which encodes a polypeptide comprising of SEQ ID NO: 4.

2. The isolated polynucleotide of claim 1, which comprises SEQ ID NO:3.

3. A recombinant vector comprising the isolated polynucleotide of claim 1.

4. A recombinant vector comprising the isolated polynucleotide of claim 2.

5. A host cell comprising the isolated polynucleotide of claim 1.

6. A host cell comprising the isolated polynucleotide of claim 2.

7. The host cell of claim 5, which is a *Corynebacterium* host cell.

8. The host cell of claim 6, which is a *Corynebacterium* host cell.

* * * * *